US010314295B2

(12) United States Patent
Kakuni et al.

(10) Patent No.: US 10,314,295 B2
(45) Date of Patent: Jun. 11, 2019

(54) MOUSE MODEL OF HYPERURICEMIA

(71) Applicant: PHOENIXBIO CO., LTD., Hiroshima (JP)

(72) Inventors: Masakazu Kakuni, Hiroshima (JP); Yumiko Iwasaki, Hiroshima (JP); Chise Mukaidani, Hiroshima (JP)

(73) Assignee: PHOENIXBIO CO., LTD., Hiroshima (JP)

( * ) Notice: Subject to any disclaimer, the term of this patent is extended or adjusted under 35 U.S.C. 154(b) by 0 days.

(21) Appl. No.: 15/308,116

(22) PCT Filed: May 7, 2015

(86) PCT No.: PCT/JP2015/063165
§ 371 (c)(1),
(2) Date: Nov. 1, 2016

(87) PCT Pub. No.: WO2015/170694
PCT Pub. Date: Nov. 12, 2015

(65) Prior Publication Data
US 2017/0055504 A1 Mar. 2, 2017

(30) Foreign Application Priority Data
May 8, 2014 (JP) ................................ 2014-097121

(51) Int. Cl.
*A01K 67/027* (2006.01)
*G01N 33/50* (2006.01)

(52) U.S. Cl.
CPC ...... *A01K 67/0271* (2013.01); *A01K 67/0276* (2013.01); *G01N 33/50* (2013.01); *G01N 33/5088* (2013.01); *A01K 2207/12* (2013.01); *A01K 2207/15* (2013.01); *A01K 2217/075* (2013.01); *A01K 2227/105* (2013.01); *A01K 2267/03* (2013.01); *A01K 2267/0362* (2013.01); *G01N 2500/00* (2013.01); *G01N 2800/708* (2013.01)

(58) Field of Classification Search
USPC ............................................ 800/3, 8, 18, 21
See application file for complete search history.

(56) References Cited

U.S. PATENT DOCUMENTS

2014/0241991 A1    8/2014  Oshimura et al.

FOREIGN PATENT DOCUMENTS

| CN | 1 698 906 | 11/2005 |
| CN | 1 698 907 | 11/2005 |
| CN | 103125439 | 6/2013 |
| EP | 1 915 904 | 4/2008 |
| EP | 2 842 417 | 3/2015 |
| JP | 2632577 | 7/1997 |
| JP | 2002-121145 | 4/2002 |
| JP | 2009-263343 | 11/2009 |
| WO | 2013/054949 | 4/2013 |
| WO | 2013/162064 | 10/2013 |

OTHER PUBLICATIONS

Wikipediea description of purine, 2018.*
Stavric (Clinical Toxicology, 1978, vol. 13, No. 1, p. 47-74).*
Wu (PNAS, 1994, 91: 742-746.*
Anzai, Endocrinology, Diabetology & Metabol., Nov. 2011, vol. 33, No. 5, p. 462-467; translation.*
Xu, CN 1698907; abstract only.*
Zuo, Shijie Linchuang Yaowu, 2010, vol. 31, No. 1, p. 18-20; abstract only.*
Qin, CN 102210787; abstract only.*
Suzuki, Nihon Univ. J. Med., 1983, vol. 25, No. 6, p. 369-380; abstract only.*
Shirakura (Annual meeting of Japan Sox. for Biosci., Biotech., and Agrochemistry, 2013, Lecture abstract, p. 458, 2A15a05), translation.*
Tateno (Am. J. Path., Sep. 2004, vol. 165, No. 3, p. 901-912).*
Kuniko JP 2009-263343 translation, 2009.*
Oshimura (WO 2013/054949) translation 2013.*
Kakuni, JP 2002-121145, 2002, translation.*
Wikipedia description of inosinic acid, 2018.*
International Preliminary Report on Patentability dated Nov. 8, 2016 in International Application No. PCT/JP2015/063165.
Extended European Search Report dated Dec. 19, 2017 in corresponding European patent application No. 15789821.4.
International Search Report dated Jul. 21, 2015 in International Application No. PCT/JP2015/063165.
Endocrinology, Diabetology & Metabolism, vol. 33, No. 5, pp. 462-467, 2011 with partial translation.
Yoshiyuki Shirakura et al., "Intake of β-cryptoxanthin reduces serum urate level in hyperuricemic model rats an mildly-hyperuricemic human subjects", Proceedings of Annual Meeting of the Japan Society for Bioscience, Biotechnology, and Agrochemistry, 2013, p. 458, Lecture No. 2A15a05, Mar. 25, 2013 with partial translation.

(Continued)

*Primary Examiner* — Michael C Wilson
(74) *Attorney, Agent, or Firm* — Wenderoth, Lind & Ponack, L.L.P.

(57) ABSTRACT

Provided is a non-human animal that is highly practical as a hyperuricenia model, the non-human animal being the following:
(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or
(b) a non-human animal obtained by producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.

6 Claims, 2 Drawing Sheets

Specification includes a Sequence Listing.

(56) References Cited

OTHER PUBLICATIONS

Edward Roddy et al., "The changing epidemiology of gout", Nature Clinical Practice Rheumatology, vol. 3, No. 8, pp. 443-449, Aug. 2007.
Takeyuki Numata et al., "Comparison of semm uric acid levels between Japanese with and without metabolic syndrome", Diabetes Research and Clinical Practice 80, pp. e1-e5, 2008.
Xiangwei Wu et al., "Hyperuricemia and urate nephropathy in urate oxidase-deficient mice", Proc. Natal. Acad. Sci., vol. 91, pp. 742-746, Jan. 1994.
B. Stavric & E.A. Nera, "Use of the Uricase-Inhibited Rat as an Animal Mode of Toxicology", Clinical Toxicology, vol. 13, No. 1, pp. 47-74, 1978.
Gout and Nucleic Acid Metabolism vol. 32, No. 1, pp. 13-18, 2008 including English Abstract.
Gout and Nucleic Acid Metabolism vol. 33, No. 1, pp. 45-49, 2009 including English Abstract.

\* cited by examiner

MOUSE MODEL OF HYPERURICEMIA

TECHNICAL FIELD

The present invention relates to a hyperuricemia model, a method for producing the same, and a method for screening for hyperuricemia therapeutic agents.

BACKGROUND ART

Uric acid is present as the final metabolite of purine base-containing substances in humans. A serum uric acid level of more than 7 mg/dL is defined as hyperuricemia, of which the causative factors include reduction in uric acid excretion, overproduction of purine base-containing substances and increase in the metabolism of purine base-containing substances. The population with hyperuricemia is on an upward trend as of 2010 (Non Patent Literature 1).

When hyperuricemia becomes chronic, the risk of developing gouty arthritis, urolithiasis, gouty nephropathy and other pathological conditions increases. Recent epidemiological studies indicate that hyperuricemia is an independent risk factor for cardiovascular and cerebrovascular diseases. In addition, hyperuricemia is a precipitating factor for diabetes mellitus and hyperlipidemia, and is considered important as a clinically useful indicator (biomarker) of various lifestyle-related diseases (Non Patent Literature 2).

Thus, hyperuricemia has an aspect of lifestyle-related disease, and the incidence of hyperuricemia and the younger onset of hyperuricemia have recently increased as well as the incidence of mild and borderline hyperuricemia, to which medication treatment is usually not applied. Accordingly, not only hyperuricemia therapeutic agents, but also relevant health foods such as dietary supplements have been developed (Patent Literature 1 and 2). The development of products other than therapeutic agents is expected to be expanded in the near future.

However, animal models for studies on hyperuricemia are difficult to produce. This is because non-primate mammals have an abundance of uricase (uricolytic enzyme) in hepatocytes, which enzyme degrades uric acid into allantoin (Non Patent Literature 3). In addition, transgenic uricase-deficient model animals result in death (Non Patent Literature 3), which is the reason why uricase deficiency in non-primate mammals cannot produce hyperuricemia.

Currently, an animal model of hyperuricemia induced by the uricase inhibitor oxonic acid (Non Patent Literature 4) is used for studies on hyperuricemia. However, this model has the disadvantage of the need for continuous administration of oxonic acid for retention of pathological conditions. Therefore, in the evaluation for hyperuricemia therapeutic agents, this animal model cannot be used without concern about the interaction of oxonic acid with a candidate therapeutic agent to be evaluated. In addition, considering that this model can produce uricase, it is dubious whether the pathological conditions of hyperuricemia in this model are equivalent to those in humans, which are naturally deficient in uricase (Non Patent Literature 5 and 6).

In addition to the oxonic acid-induced hyperuricemia model, high-purine diet-induced hyperuricemia rodent models are known. These models can be produced by dietary administration or oral gavage administration of purines such as inosinic acid, hypoxanthine and RNA. However, since these dietary hyperuricemia mammal models have uricase, the plasma uric acid concentrations are often not sufficiently high. For this reason, these models are usually used with oxonic acid administration, which is disadvantageous as with the case of the oxonic acid-induced animal model.

Non Patent Literature 7 and 8 teach that chimeric mice produced by transplantation of human hepatocytes to immunodeficient mice with liver dysfunction may develop hyperuricemia and can be a hyperuricemia model producible without purine base-rich substance administration or chemical administration.

However, the development of hyperuricemia is observed in only some of the chimeric mice according to NOB Patent Literature 7 and 8. In addition, these chimeric mice have low weights and thus difficult to use as an experimental animal.

CITATION LIST

Patent Literature

Patent Literature 1:
  JP-A 2002-121145; Japanese Patent No. 3768795
Patent Literature 2:
  JP-A 2009-263343; Japanese Patent No. 5437672

Non Patent Literature

Non Patent Literature 1:
  Nat Clin Pract Rheumatol 3: 443-449, 2007
Non Patent Literature 2:
  Diabetes Res Clin Pract 80: e1-e5, 2008
Non Patent Literature 3:
  Proc. Natl. Acad. Sci. 91: 742-746, 1994
Non Patent Literature 4:
  Clin. Toxicol. 13: 47-74, 1978
Non Patent Literature 5:
  Gout and Nucleic Acid Metabolism 32: 13-18, 2008
Non Patent Literature 6:
  Gout and Nucleic Acid Metabolism 33: 45-49, 2009
Non Patent Literature 7:
  Gout and Nucleic Acid Metabolism, vol. 32, No. 1, pp. 13-18
Non Patent Literature 8:
  Gout and Nucleic Acid Metabolism, vol. 33, No. 1, pp. 45-49

SUMMARY OF INVENTION

Technical Problem

An object of the present invention is to provide a practical hyperuricemia model, a method for producing this model, and a method for screening for hyperuricemia therapeutic agents using the model.

Solution to Problem

The present inventors conducted extensive research to achieve the above-mentioned object, and as a result, made the following findings.

That is, a non-human animal having an increased level of plasma uric acid can be obtained in a highly efficient manner by administration of a purine base-containing substance to (a) a primary chimeric non-human animal produced by transplantation of human hepatocytes to an immunodeficient non-human animal with liver dysfunction, or (b) a serially transplanted chimeric non-human animal produced by transplantation of the human hepatocytes grown in the body of the primary chimeric non-human animal to an immunodeficient non-human animal with liver dysfunction.

The thus-obtained non-human animal having an increased level of plasma uric acid has a sufficient body weight and sufficient viability, and meets the requirements for experimental use.

The present invention has been completed based on the above findings, and provides the following hyperuricemia model, the following method for producing the same, and the following method for screening for hyperuricemia therapeutic agents.

[1] A hyperuricemia model being the following non-human animal:
(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or
(b) a non-human animal obtained by producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.
[2] The hyperuricemia model according to the above [1], wherein the hyperuricemia model has a liver with a human hepatocyte replacement rate of 50% or more.
[3] The hyperuricemia model according to the above [1] or [2], wherein the purine base-containing substance is administered to the primary chimeric non-human animal or the serially transplanted chimeric non-human animal by free-feeding with a diet containing about 1 to 10% by weight of the purine base-containing substance for about 7 to 28 days.
[4] The hyperuricemia model according to the above [1] or [2], wherein the purine base-containing substance is administered to the primary chimeric non-human animal or the serially transplanted chimeric non-human animal in a total amount of 30 to 350 g/kg body weight.
[5] The hyperuricemia model according to any of the above [1] to [4], wherein the hyperuricemia model has a body weight that is 80% or more of that of an animal of the same species.
[6] The hyperuricemia model according to any of the above [1] to [5], wherein the hyperuricemia model has a plasma or serum uric acid concentration of 4 mg/dL or more.
[7] A method for producing a hyperuricemia model,
(c) The method comprising producing a primary chimeric non-human animal by transplantation of human hepatocytes to an immunodeficient non-human animal with liver dysfunction; and subsequently administering a purine base-containing substance to the primary chimeric non-human animal, or
(d) the method comprising producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.
[8] The method according to the above [7], wherein the purine base-containing substance is administered to the primary chimeric non-human animal or the serially transplanted chimeric non-human animal which has a liver with a human hepatocyte replacement rate of 50% or more.
[9] The method, according to the above [7] or [8], wherein the purine base-containing substance is administered to the primary chimeric non-human animal or the serially transplanted chimeric non-human animal by free-feeding with a diet containing about 1 to 10% by weight of the purine base-containing substance for about 7 to 28 days.
[10] The method according to the above [7] or [8], wherein the purine base-containing substance is administered to the primary chimeric non-human animal or the serially transplanted chimeric non-human animal in a total amount of 30 to 350 g/kg body weight.
[11] A method for screening for hyperuricemia therapeutic agents, the method comprising the steps of:
(1) administering test substances to the following non-human animal:
(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or
(b) a non-human animal obtained by producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal,
(2) comparing plasma or serum uric acid concentrations before and after the administration of each test substance, and
(3) selecting, from among the test substances, the one capable of significantly lowering the plasma or serum uric acid concentration.
[12] The method according to the above [11], wherein the non-human animal to which the test substance is to be administered has a liver with a human hepatocyte replacement rate of 50% or more.
[13] The method according to the above [11] or [12], wherein the purine base-containing substance is administered to the primary chimeric non-human animal or the serially transplanted chimeric non-human animal by free-feeding with a diet containing about 1 to 10% by weight of the purine base-containing substance for about 7 to 28 days.
[14] The method according to the above [11] or [12], wherein the purine base-containing substance is administered to the primary chimeric non-human animal or the serially transplanted chimeric non-human animal in a total amount of 30 to 350 g/kg body weight.

[15] Use of a non-human animal as a hyperuricemia model, the non-human animal being the following:
(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or
  (b) a non-human animal obtained by producing a serially transplanted chimeric non-human animal via two steps, a first step being a step of producing a primary chimeric non-human, animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.
[16] The use according to the above [15], wherein the non-human animal (a) or (b) has a liver with a human hepatocyte replacement rate of 50% or more.
[17] The use according to the above [15] or [16], wherein the purine base-containing substance is administered to the primary chimeric non-human animal or the serially transplanted chimeric non-human animal by free-feeding with a diet containing about 1 to 10% by weight of the purine base-containing substance for about 7 to 28 days.
[18] The use according to the above [15] or [16], wherein the purine base-containing substance is administered to the primary chimeric non-human animal or the serially transplanted chimeric non-human animal in a total amount of 30 to 350 g/kg body weight.
[19] The use according to any of the above [15] to [18], wherein the non-human animal (a) or (b) has a body weight that is 80% or more of that of an animal of the same species.
[20] The use according to any of the above [15] to [19], wherein the non-human animal (a) or (b) has a plasma or serum uric acid concentration of 4 mg/dL or more.
[21] Use of a non-human animal for production of a hyperuricemia model, the non-human animal being the following:
(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or
(b) a non-human animal obtained by producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.
[22] The use according to the above [21], wherein the non-human animal (a) or (b) has a liver with a human hepatocyte replacement rate of 50% or more.
[23] The use according to the above [21] or [22], wherein the purine base-containing substance is administered to the primary chimeric non-human animal or the serially transplanted chimeric non-human animal by free-feeding with a diet containing about 1 to 10% by weight of the purine base-containing substance for about 7 to 28 days.
[24] The use according to the above [21] or [22], wherein the purine base-containing substance is administered to the primary chimeric non-human animal or the serially transplanted chimeric non-human animal in a total amount of 30 to 350 g/kg body weight.
[25] The use according to any of the above [21] or [24], wherein the non-human animal (a) or (b) has a body weight that is 80% or more of that of an animal of the same species.
[26] The use according to any of the above [21] or [25], wherein the non-human animal (a) or (b) has a plasma or serum uric acid concentration of 4 mg/dl. or more.

Advantageous Effects of Invention

The model of the present invention is a chimeric animal in which the whole or a part of the liver is repopulated with human hepatocytes. Human hepatocytes are naturally deficient in uricase, and thus in the model of the present invention, the production of uricase is suppressed. In addition, a purine base-containing substance is administered in the course of the production of the model of the present invention, and thus the model has a sufficiently increased level of plasma uric acid. Moreover, this model has a sufficient body weight and sufficient viability as compared with conventional chimeric animals which have not been subjected to administration of a purine base-containing substance, and meets the requirements for experimental use. Furthermore, the model of the present invention does not necessitate administration of oxonic acid or the like during use, and thus in the evaluation for hyperuricemia therapeutic agents, this model can be used without concern about the interaction of oxonic acid and a candidate therapeutic agent to be evaluated. Purine bases are physiological substances and are also food ingredients, and thus is very rarely a cause for concern about the interaction with a candidate therapeutic agent to be evaluated. The model of the present invention is deficient in uricase, and thus manifests pathological conditions equivalent to those of hyperuricemia in humans. Therefore, this model can be a model of human hyperuricemia, and is suitable for use in screening for hyperuricemia therapeutic agents, studies on the mechanism of hyperuricemia, etc.

In addition, according to the method of the present invention, which comprises administering a purine base-containing substance to a chimeric animal in which the whole or a part of the liver is repopulated with human hepatocytes, hyperuricemic animals can be obtained with very high probability.

DESCRIPTION OF EMBODIMENTS

Figure 1:
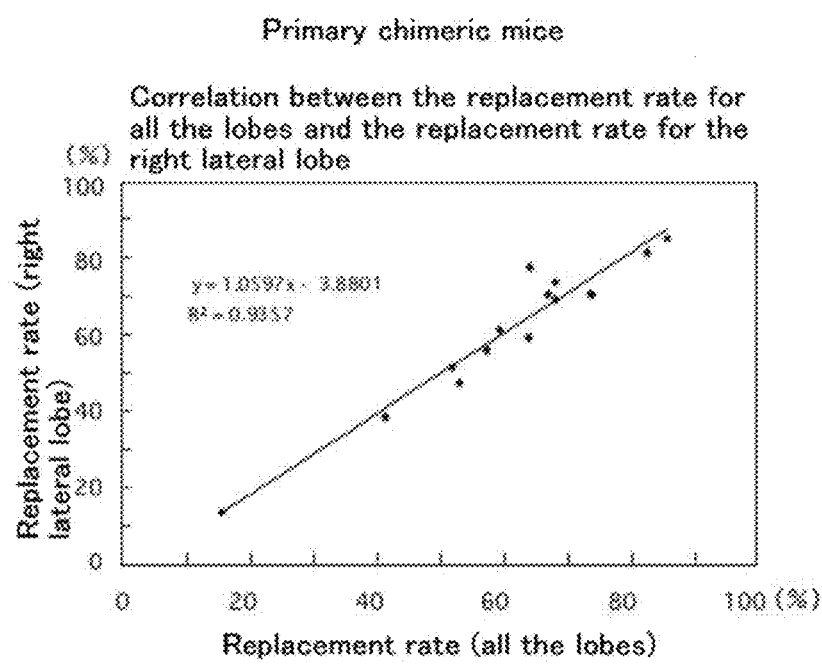
FIG. 1 shows the correlation between the human hepatocyte replacement rate determined for all the seven lobes of the liver and the replacement rate determined for the right lateral lobe in primary chimeric mice.

Hereinafter, the present invention will be described in detail.

(I) Method For Producing Hyperuricemia Model

The method of the present invention for producing a hyperuricemia model is the following:

(c) the method comprising producing a primary chimeric non-human animal by transplantation of human hepatocytes to an immunodeficient non-human animal with liver dysfunction; and subsequently administering a purine base-containing substance to the primary chimeric non-human animal, or (d) the method comprising producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.

Non-Human Animal

In the present invention, the non-human animal (hereinafter sometimes abbreviated to "animal") is preferably a mammal, and more preferably a rodent. Examples of the rodent include murine rodents such as mice and rats, guinea pigs, squirrels and hamsters, and among these, mice and rats, which are widely used as experimental animals, are easier to use.

Immunodeficient Non-Human Animal With Liver Dysfunction

The immunodeficient non-human animal with liver dysfunction is a non-human animal whose immune system is so compromised as not to mount a rejection response against cells from animals of a different species and whose innate hepatocytes are impaired. Transplantation of human hepatocytes to such an animal, whose innate hepatocytes are impaired, will enable the maintenance of liver functions by the transplanted human hepatocytes and the animal will present an accurate reflection of in vivo functions of human hepatocytes. In addition, the transplanted human hepatocytes will easily grow.

The immunodeficient animal with liver dysfunction can be produced by subjecting an animal to both immunodeficiency-inducing treatment and liver dysfunction-inducing treatment. Examples of the liver dysfunction-inducing treatment include administration of liver dysfunction inducers such as carbon tetrachloride, yellow phosphorus, D-galactosamine, 2-acetylaminofluorene and pyrrolodine alkaloids; and surgical removal of part of the liver. Examples of the immunodeficiency-inducing treatment include administration of immunosuppressants and thymectomy.

The immunodeficient animal with liver dysfunction can also be produced by liver dysfunction-inducing treatment of a genetically immunodeficient animal. Examples of the genetically immunodeficient animal include an animal which has severe combined immunodeficiency (SCID), which is characterized by T-cell failure; an animal which has absent T-cell functions due to hereditary athymia; and an animal whose RAG2 gene has been knocked out by a known gene targeting method (Science, 244: 1298-1292, 1989). The specific examples include a SCID mouse, a NOG mouse, a NUDE mouse, a RAG2 knockout mouse, and genetically immunodeficient rats similar in nature to these mice.

The immunodeficient animal with liver dysfunction can also be produced by immunodeficiency-inducing treatment of an animal genetically having liver dysfunction. Examples of the animal genetically having liver dysfunction include a transgenic animal produced with the use of a liver dysfunction-inducing protein gene inserted under the control of an enhancer and/or a promoter for a protein specifically expressed in hepatocytes according to a known transgenic method (Proc. Natl. Acad. Sci. USA 77; 7380-7384, 1980). In such an animal, the liver dysfunction-inducing protein is specifically expressed in the liver, and liver dysfunction is manifested. Examples of the protein specifically expressed in the liver include serum albumin, cholinesterase and Hageman factor. Examples of the liver dysfunction-inducing protein include urokinase plasminogen activator (uPA), tissue plasminogen activator (tPA) and human herpes simplex virus type 1 thymidine kinase (HSV-tk) (in the case of HSV-tk, liver dysfunction can be induced by ganciclovir administration). The animal genetically having liver dysfunction can also be obtained by knockout of a gene responsible for a liver function, such as a fumarylacetoacetate hydrolase gene.

Moreover, the immunodeficient animal with liver dysfunction can also be produced by crossing of a genetically immunodeficient animal to an animal genetically having liver dysfunction, the two types of animals being of the same species. The animal genetically having immunodeficiency and liver dysfunction is preferably an animal which is homozygous for a liver dysfunction-inducing gene. In such a homozygous animal, its own normal hepatocytes hardly proliferate, and thus do not interfere with proliferation of human hepatocytes. However, such a homozygous animal can be obtained with a probability of only ¼ by crossing of the corresponding hemizygous animals.

On the other hand, a genetically immunodeficient animal with liver dysfunction which is hemizygous for a liver dysfunction-inducing gene ("immunodeficient animal hemizygous for liver dysfunction") can be obtained with a probability of ½ by crossing of hemizygous animals with liver dysfunction or crossing of a hemizygous animal with liver dysfunction to a genetically immunodeficient animal, and thus low-cost production is possible.

Examples of known immunodeficient non-human animals with liver dysfunction include a uPA/SCID mouse (Examples of the present application), a uPA/RAG-2 mouse ("HEPATOLOGY 2001, 33, 981-988" and "Journal of Hepatology, 42 (2005) 54-60"), a NOD/SCID mouse, a BALB/c-Rag2/Il2rg mouse, a NOD/SCID/B2m mouse, a NOD/SCID/Tg(HLA-A2) mouse, a NOD/SCID/Il2rg mouse, a NOD/Ragl/Il2rg mouse, a NOD/Ragl mouse, a NOD/Ragl/Prfl mouse, a NOD/Ragl/Tg(SOD1-GA) 1Gur mouse, a NOD/Ragl/Ins2$^{Akita}$ mouse, a NOD-Ragl/Dmd$^{mdx-SCv}$ mouse (for those described thus far, see "NATURE REVIEWS, Vol. 7, February 2007, 118-130"), a uPA/NOG mouse ("Biochemical and Biophysical Research Communications, 377 (2008) 248-252"), a TK-NOG mouse (WO 2010/082385 and Japanese Patent No. 5073836), and a Fah/Rag2/Il2rg mouse ("Nature Biotechnology, Vol. 25, No. 8, August 2007, 903-910").

As for animals other than mice, an X-SCID rat, which is a knockout rat with immunodeficiency, is known ("Plos one, January 2010, Vol. 5, Issue 1, e8870"). It is also known that administration of a hepatocyte growth inhibitor, retrorsine, to a partially hepatectomized rat can induce liver dysfunction with such severity that transplanted hepatocytes can grow ("American Journal of Pathology, Vol. 158, No. 1, January 2001"). That is, administration of retrorsine to a partially hepatectomized X-SCID rat can lead to production of an immunodeficient rat with liver dysfunction.

In addition, it is also known that transplantation of human hepatocytes to a retrorsine-administered juvenile rat in combination with administration of an immunosuppressant allows the growth of the human hepatocytes (Program and Abstracts of the 36th Regular Scientific Meeting of the Japan Society for Organ Preservation and Biology Vol. 16, No. 1, 2009; and Program and Abstracts of the 15th Annual Meeting of the Japanese Society for the Research of Hepatic Cells, 2008). This report indicates that administration of an immunosuppressant to a retrorsine-administered juvenile rat can lead to production of an immunodeficient rat with liver dysfunction.

Human Hepatocytes

The human hepatocytes to be used for transplantation may be ones isolated from normal human hepatic tissue by a method known in the art, such as collagenase perfusion. The isolated hepatocytes may be cryopreserved. The cryopreserved hepatocytes can be used after thawed.

The age of a human subject for the isolation of hepatocytes is not particularly limited. For example, when human hepatocytes from child donors under 14 years old are used for transplantation, a high rate of human hepatocyte replacement can be attained.

The human hepatocytes to be used for transplantation are preferably proliferative hepatocytes having in vivo highly proliferative ability. In the present invention, "proliferative human hepatocytes" refer to human hepatocytes that form a colony as a population derived from a single cell under culture conditions (in vitro) and grow in such a manner that the colony expands. This growth is also referred to as "clonal growth" because the colony is derived from a single cell. Such cells are capable of increasing in number through passage culture.

An example of the proliferative human hepatocytes that can be used is human small hepatocytes invented by the present inventor Chise Mukaidani et al. (JP-A 08-112092; Japanese Patent No. 3266766; U.S. Pat. No. 6,004,810, JP-A 10-179148; Japanese Patent No. 3211941, JP-A 07-274951; Japanese Patent No. 3157984, JP-A 9-313172; and Japanese Patent No. 3014322). Since these human small hepatocytes have a highly proliferative ability, they can grow rapidly in the body of a recipient and quickly form a human hepatocyte population capable of performing normal liver functions.

Such small hepatocytes can be isolated not only by a method using centrifugation as described in the abovementioned publications, but also with a cell sorter such as an elutriator and FACS. Alternatively, the small hepatocytes can be isolated by using a monoclonal antibody that specifically recognizes hepatocytes growing with colony expansion. Other examples of the human hepatocytes that can be used in the present invention include human hepatocytes grown in vitro, cryopreserved hepatocytes, hepatocytes immortalized by introducing a telomerase gene or the like, and a mixture of any of these hepatocytes with nonparenchymal cells.

Production of Primary Chimeric Animal

The above-described human hepatocytes can be transplanted into the liver via the spleen of an immunodeficient animal with liver dysfunction. Alternatively, the human hepatocytes can be transplanted directly into the liver via the portal vein. The number of the human hepatocytes to be transplanted can be about 1 to 2,000,000, and preferably about 100,000 to 1,000,000.

The sex of the immunodeficient animal with liver dysfunction is not particularly limited. The age in days of the immunodeficient animal with liver dysfunction at the time of transplantation is not particularly limited, but the animal to be used is preferably aged about 0 to 40 days, particularly preferably about 8 to 40 days. This is because human hepatocytes transplanted to the animal at a younger age can more actively grow along with the animal's growth.

After transplantation, the recipient animal is maintained or raised in the usual manner. The animal is maintained or raised until the rate of human hepatocyte replacement reaches about 50% or more, more preferably about 60% or more, still more preferably about 70% or more, yet still more preferably about 80% or more, and particularly preferably about 90% or more. When such levels are reached, the production of uricase is sufficiently suppressed.

A higher rate of human hepatocyte replacement is preferable for increasing the plasma uric acid concentration. However, even when the replacement rate is slightly low, the method of the present invention comprising administering a purine base-containing substance enables a sufficient increase in the plasma uric acid concentration. Accordingly, the rate of human hepatocyte replacement can be about 90% or less, about 80% or less, about 70% or less, about 65% or less, about 60% or less, about 55% or less, or about 50% or less although it varies with the dosage of the purine base-containing substance. When the replacement rate is as specified above, a hyperuricemia model having a sufficient body weight and sufficient viability can be obtained.

When the period for maintaining or raising the recipient animal after transplantation is, for example, about 20 to 200 days, a primary chimeric non-human animal in which the rate of human hepatocyte replacement is about 50% or more can usually be obtained. In the case of mice, after a mouse to which about $7.5 \times 10^5$ human hepatocytes have been transplanted is maintained for about 40 to 120 days, the rate of human hepatocyte replacement reaches about 50% or more.

The rate of human hepatocyte replacement can be reduced by decreasing the number of human hepatocytes to be transplanted or by shortening a period for maintaining or raising an animal after transplantation of human hepatocytes (within the above range). Those skilled in the art can adjust the rate of human hepatocyte replacement to any value through experiments.

The rate of human hepatocyte replacement can be determined by, for example, hematoxylin and eosin staining of sections sliced from the liver of the chimeric non-human animal, for example, the right lateral lobe of the liver. It is evident from the Reference Example shown below that the replacement rate determined for the right lateral lobe of the liver is equivalent to the replacement rate determined for all the lobes of the liver.

<Reference Example>

The experiment shown below clearly demonstrates a high correlation between the replacement rate determined for all the seven lobes of the liver and the replacement rate determined for the right lateral lobe in chimeric mice. Fourteen chimeric mice were generated by transplantation of frozen human hepatocytes Lot. NLR (from a 12-year-old boy)

purchased from In Vitro Technology. From each chimeric mouse (46 to 102 days after transplantation), histological sections of all the seven hepatic lobes were prepared, and the rate of human hepatocyte replacement was determined as the percentage of the human cytokeratin 8/18 antibody-positive area.

The correlation between the replacement rate determined for the whole liver, that is, for all the seven hepatic lobes, and the replacement rate determined for the right lateral lobe was analyzed, and as a result, the correlation coefficient was calculated to be $R^2=0.9357$. The correlation diagram is shown in FIG. 1.

The blood human albumin concentration of the chimeric animal serves as an indicator of the rate of human hepatocyte replacement. The blood human albumin concentration varies with the species or lineage of the animal, but basically, when the blood human albumin concentration of the chimeric animal is about 3.7 mg/mL or more, the rate of human hepatocyte replacement is usually about 50% or more. The blood human albumin concentration of the chimeric animal is preferably about 5.2 mg/mL or more, more preferably about 7.4 mg/mL or more, still more preferably about 10.6 mg/mL or more, and particularly preferably about 15.2 mg/mL or more.

The blood human albumin concentration can be about 15.2 mg/mL or less, about 10.6 mg/mL or less, about 7.4 mg/mL or less, about 6.2 mg/mL or less, about 5.2 mg/mL or less, about 4.4 mg/mL or less, or about 3.7 mg/mL or less.

The rates of human hepatocyte replacement in the primary chimeric non-human animal and in the serially transplanted chimeric non-human animal described later do not change or do not substantially change before and after the administration of the purine base-containing substance.

In the primary chimeric animal produced as described above, the production of uricase is sufficiently suppressed. Optionally, the human hepatocytes grown in the body of the primary chimeric animal may be further transplanted to an immunodeficient animal of the same species with liver dysfunction for production of a serially transplanted chimeric animal. Also in the serially transplanted chimeric animal, which is produced by one or more rounds of transplantation, the production of uricase is sufficiently suppressed.

Production of Serially Transplanted Chimeric Animal

The human hepatocytes grown in the body of the primary chimeric animal can be recovered by, for example, collagenase treatment of the hepatic tissue of the primary chimeric animal. Due to higher cytotoxicity of collagenase against non-human animal hepatocytes than against human hepatocytes, the collagenase treatment can give selective damage to innate hepatocytes of the chimeric animal by adjustment of the duration of the collagenase treatment, and thus allows isolation of substantially only human hepatocytes. The duration of the collagenase treatment varies with the ratio of human hepatocytes and non-human hepatocytes. For example, in the case where the rate of human hepatocyte replacement is about 50 to 100%, that is, in the case where the blood albumin concentration is about 4 to 20 mg/mL for mice, the treatment is performed with an about 0.01 to 0.1% by weight collagenase solution for about 5 to 30 minutes. In the hepatic cells thus recovered from the hepatic tissue, not only the human hepatocytes grown in the body of the chimeric animal, but also a small number of hepatic non-parenchymal cells are contained. In addition, a small number of innate hepatocytes of the chimeric animal are also contained.

The recovered hepatic cells may be used directly for transplantation. Alternatively, before use for transplantation, the purity of the human hepatocytes may be increased with the use of a monoclonal antibody that specifically recognizes human hepatocytes or mouse hepatocytes. In the case where a human hepatocyte-specific antibody is used for the reaction with the recovered hepatic cells, the population of reacted cells is recovered with a fluorescence-activated cell sorter (FACS) or a magnetic activated cell sorter (MACS). In the case where a mouse hepatocyte-specific antibody is used for the reaction with the recovered hepatic cells, the population of non-reacted cells is recovered with FACS or MACS.

Examples of the monoclonal antibody that specifically recognizes human hepatocytes include one obtained from the culture of hybridoma cell line K8216, which has been established by the present inventors (deposited with International Patent Organism Depositary (IPOD), National Institute of Advanced Industrial Science and Technology (AIST) (Tsukuba Center, Central 6, 1-1-1 Higashi, Tsukuba, Ibaraki, Japan) under FERM P-18751 on Mar. 6, 2002, and internationally deposited with the same depositary under FERM EP-8333 on Mar. 20, 2003), as well as one recovered from peritoneal fluid after intraperitoneal injection of the above hybridoma cells into a mouse. Examples of the monoclonal antibody that specifically recognizes mouse hepatocytes include 66Z antibody ("Drug Metab. Pharmacokinet., Vol. 25, No. 6: 539-550, 2010"). Particularly, examples of the monoclonal antibody that specifically recognizes human proliferative hepatocytes include one obtained from the culture of hybridoma cell line K8223, which has been established by the present inventors (deposited with International Patent Organism Depositary (IPOD), National Institute of Advanced Industrial Science and Technology (AIST) under FERM P-18752 on Mar. 6, 2002, and internationally deposited under FERM BP-8334 on Mar. 20, 2003), as well as one recovered from peritoneal fluid after intraperitoneal injection of the above hybridoma cells into a mouse.

The human hepatocytes grown in the body of the primary chimeric animal are transplanted to a new recipient or another immunodeficient non-human animal with liver dysfunction for production of a serially transplanted chimeric animal. The immunodeficient non-human animal with liver dysfunction as a new recipient and the non-human animal used for the production of the primary chimeric animal may be animals of the same or different species, but are preferably animals of the same species. The "animals of the same species" refers to mice when the animal used for the production of the primary chimeric animal is a mouse, or refers to rats when the animal used for the production of the primary chimeric animal is a rat.

In the case where the non-human animal used for the production of the primary chimeric animal and the immunodeficient non-human animal with liver dysfunction as a new recipient to be subjected to the transplantation of human hepatocytes from the primary chimeric animal are of different species, both the animals are preferably rodents, and more preferably murine rodents. In an example, the non-human animal used for the production of the primary chimeric animal is a mouse, and the immunodeficient non-human animal with liver dysfunction as a new recipient to be subjected to the transplantation of human hepatocytes from the primary chimeric animal is a rat. In another example, the non-human animal used for the production of the primary chimeric animal is a rat, and the immunodeficient non-human animal with liver dysfunction as a new recipient to be subjected to the transplantation of human hepatocytes from the primary chimeric animal is a mouse.

The number of rounds of transplantation for the production of the serially transplanted chimeric animal may be one or two or more. For example, in the case of 3 rounds, the human hepatocytes grown in the body of the primary chimeric animal are transplanted to an immunodeficient animal with liver dysfunction as a new recipient for production of a serially transplanted chimeric animal, and the human hepatocytes grown in the body of this serially transplanted chimeric animal are transplanted to another immunodeficient animal with liver dysfunction as a new recipient for production of another serially transplanted chimeric animal.

The cell delivery route and cell number for the transplantation of the human hepatocytes recovered from the primary chimeric animal into the liver of the non-human animal are the same as those in the case of the production of the primary chimeric animal. The age in days and sex of the recipient non-human animal are also the same as those in the case of the production of the primary chimeric animal.

After the recipient animal is maintained or raised in the usual manner, a serially transplanted chimeric animal in which some or all of the innate hepatocytes have been replaced by human hepatocytes can be obtained.

The rate of human hepatocyte replacement and the serum human albumin concentration are the same as those described for the primary chimeric mouse.

Administration of Purine Base-Containing Substance

The primary chimeric animal or the serially transplanted chimeric animal produced as described above is subjected to administration of a purine base-containing substance.

Examples of the purine base-containing substance that can be used include substances consisting of purine bases, for example, purine; nucleic acid bases such as adenine, guanine and hypoxanthine; and alkaloids such as xanthine, theobromine, caffeic acid, uric acid and isoguanine. In addition, purine base-containing ribonucleotides such as adenylic acid, guanylic acid and inosinic acid can also be used. Among them, ribonucleotides are preferred, and inosinic acid is more preferred.

The purine base-containing substance may be administered in the diet or administered forcibly (particularly, administered by oral gavage).

In the case where the purine base-containing substance is administered in the diet, the dosage regime can be designed as follows:

free-feeding with a diet containing about 1 to 10% by weight of the purine base-containing substance is continued for about 7 to 28 days (particularly, for 14 to 28 days);
free-feeding with a diet containing about 1 to 10% by weight of the purine base-containing substance is continued for about 5 to 10 days (particularly, for about 7 days); or
free-feeding with a diet containing about 0.1 to 5% by weight (particularly, about 1% by weight) of the purine base-containing substance is continued for 7 to 28 days (particularly, for about 7 to 14 days). At any of the above dosage regimen, a sufficiently high level of plasma uric acid can be attained.

In any case, the dosage of the purine base-containing substance is preferably 30 g/kg body weight or more, more preferably 50 g/kg body weight, or more, still more preferably 80 g/kg body weight or more, and particularly preferably 88 g/kg body weight or more as a total amount. When the dosage is as specified above, a sufficiently high level of plasma uric acid can be attained and animal's weight loss can be prevented.

The dosage of the purine base-containing substance is preferably 350 g/kg body weight or less, more preferably 300 g/kg body weight or less, still more preferably 250 g/kg body weight or less, and particularly preferably 200 g/kg body weight or less as a total amount. When the dosage is as specified above, animal's weight loss can be prevented.

For example, in the case of mice, free-feeding with a diet containing about 1 to 10% by weight of the purine base-containing substance corresponds to administration of the purine base-containing substance in an amount of about 1.3 to 11.5 g/kg body weight per day. In addition, about 14 to 28 days of free-feeding with a diet containing about 1 to 10% by weight of the purine base-containing substance corresponds to administration of the purine base-containing substance in a total amount of about 88 to 260 g/kg body weight.

The dosage of the purine base-containing substance can be adjusted so that the plasma uric acid concentration will be increased to 1.3-fold or more, particularly 1.5-fold or more, more particularly 5-fold or more, still more particularly 8-fold or more, yet still more particularly 9.8-fold or more, and yet still more particularly 10-fold or more.

(II) Hyperuricemia Model

By administering the purine base-containing substance to the chimeric non-human animal as described above, the hyperuricemia model of the present invention, in which the blood uric acid concentration is sufficiently increased, can be obtained.

That is, the hyperuricemia model of the present invention is the following non-human animal:

(a) a non-human animal obtained by producing a primary chimeric non-human animal by transplantation of human hepatocytes to an immunodeficient non-human animal with liver dysfunction; and subsequently administering a purine base-containing substance to the primary chimeric non-human animal, or (b) a non-human animal obtained by producing a serially transplanted chimeric non-human animal via two steps, a first step being a step of producing a primary chimeric non-human animal by transplantation of human hepatocytes to an immunodeficient non-human animal with liver dysfunction, a second step being a step of transplanting the human hepatocytes grown in the body of the primary chimeric non-human animal to an immunodeficient non-human animal with liver dysfunction, the second step being performed one or more times; and subsequently administering a purine base-containing substance to the serially transplanted chimeric non-human animal.

The present invention includes a method using the above non-human animal (a) or (b) as a hyperuricemia model.

Plasma Uric Acid Concentration

In hyperuricemia model rats currently used for screening for hyperuricemia therapeutic agents, studies on hyperuricemia, etc., the plasma or serum uric acid concentration is about 2 to 3 mg/dL. For example, "Bioorg Med Chem Lett, 2012 Jan 1, Vol. 22, No. 1" and "Jpn. J. Pharmacol, 1980, Vol. 30" report that rats having a plasma or serum uric acid concentration of about 2 to 3 mg/dL were obtained by oxonic acid administration.

On the other hand, in the hyperuricemia model of the present invention, the plasma or serum uric acid concentration can be 4 mg/dL or more.

Body Weight

The hyperuricemia model of the present invention is also characterized in that body weight loss is suppressed. While the average weight of an animal of the same species as the hyperuricemia model is 19.4 g, the average weight of the hyperuricemia model can be, for example, about 80% or more, particularly about 85% or more, more particularly about 90% or more, even more particularly about 92% or mere of that average weight.

(III) Method For Screening For Hyperuricemia Therapeutic Agents

The method of the present invention for screening for hyperuricemia therapeutic agents comprises the steps of:
(1) administering test substances to the non-human animal (a) or (b), which has an increased level of blood uric acid as described above,
(2) comparing plasma or serum uric acid concentrations before and after the administration of each test substance, and
(3) selecting, from among the test substances, the one capable of significantly lowering the plasma or serum uric acid concentration.

The kind of the test substance is not particularly limited. Examples of the test substance include proteins, peptides, nucleic acids, carbohydrates, lipids, low-molecular-weight organic compounds, low-molecular-weight inorganic compounds, fermentation products, cell extracts, nuclear extracts from cells, plant extracts, animal tissue extracts and microbial culture supernatants.

The frequency of the administration of the test substance is not particularly limited, but single administration is usually sufficient. The dosage is not limited because it varies with the kind of the test substance. In one example, the dosage can be determined based on the maximum allowable dose of the test substance or on the time-course change in blood concentration of the test substance.

The administration route varies with the kind of the test substance, and the examples include oral administration (e.g., oral gavage administration, dietary administration, etc.), intravenous administration, subcutaneous administration, intraperitoneal administration, percutaneous administration and intramuscular administration. Among them, oral administration is preferred, and oral gavage administration is more preferred.

The plasma or serum uric acid concentration can be measured with DRI-CHEM 7000 (FUJIFILM Corporation, Tokyo).

When the administration of the test substance results in a significant reduction of the plasma or serum uric acid concentration, the test substance can be determined to be a potential candidate as a hyperuricemia therapeutic agent. In the present invention, the term "significant" means that a significant difference is detected between groups of 3 or more model animals each based on a t-test with a significance level of 0.05%.

When the administration of the test substance results in reduction of the plasma uric acid concentration to, for example, 70% or less, 50% or less, preferably 45% or less, more preferably 40% or less of the level before administration, the test substance can be determined to be a potential candidate as a hyperuricemia therapeutic agent.

EXAMPLES

Hereinafter, the present invention will be illustrated in more detail by examples, but the present invention is not limited thereto.
(1) Production of Primary Chimeric Mice
(1-1) Production of Immunodeficient Mice With Liver Dysfunction Two rounds of backcrossing of uPA-Tg mice (hemizygote, +/−) to SCID-bg mice produced mice with the genotype uPA-Tg(+/−)SCID(+/+). Sperm was collected from the male uPA-Tg(+/−) SCID(+/+) mice and used for in vitro fertilization of unfertilized eggs of SCID mice (homozygote, +/+). The fertilized eggs were transferred to a surrogate uterus. From among newborn mice, the ones carrying the Tg gene were selected and allowed to naturally mate. As a result, mice with the two phenotypic traits, i.e., uPA-Tg (+/−)/SCID(+/+) mice were produced. To distinguish between uPA-Tg(+/−) and uPA-Tg(−/−), genomic PCR was performed using transgene-specific sequences as primers.
Forward Primer

```
                                         (SEQ ID NO: 1)
5'-GGGCGGCGGTACCGATCCTGAGAACTTCAGGGTGAG-3'

Reverse primer
                                         (SEQ ID NO: 2)
5'-GGGCGGCGGTACCAATTCTTTGCCAAAATGATGAGA-3'
```

To distinguish among SCID(+/+), SCID(+/−) and SCID (−/−), PCR-RFLP was performed.

Next, crossing of the obtained uPA-Tg(+/−)/SCID(+/+) mice produced uPA-Tg(+/+)/SCID(+/+) mice and uPA-Tg (+/−)/SCID(+/+) mice. To distinguish between uPA-Tg(+/+) and uPA-Tg(+/−), southern blotting was performed. An about 5 mm of the tail was cut off from each mouse at the age of 8 to 10 days and lysed with a solution containing SDS and proteinase K. Protein components in the lysate were removed by phenol and chloroform extraction. After RNA degradation with DKase-free RNase A, isopropanol was added for precipitation of high-molecular-weight genomic DNA. The precipitated genomic DNA was washed with 70% ethanol, air-dried and dissolved in TE. Five micrograms each of the genomic DNA extracted from each tail sample and the genomic DNAs of positive and negative controls were completely digested with EcoR1. The resulting DNA fragments were separated by agarose electrophoresis and then transferred to a nylon membrane. A uPA cDNA probe/ TA was digested with restriction enzyme EcoR1 for preparation of DNA fragments (379 bp) suitable as the probes for Southern hybridization. The DNA fragments were then $^{32}$P-labeled by random primed labeling. The DNA fragments transferred to the nylon membrane were hybridized with the RI-labeled uPA cDNA probes. The nylon membrane was washed for removal of nonspecifically bound probes, and exposed to an X-ray film for detection of the radioactive signal from the foreign gene inserted in each mAlb-uPA-Int2 Tg mouse candidate. A signal specific to a 1.5-kb fragment from the wild-type allele and a signal specific to a 0.4-kb fragment from the mutant allele (wt: 1.5 kb) were detected, and based on the signals, the mAlb-uPA-Int2 Tg mouse candidates were genotyped.

(1-2) Transplantation of Human Hepatocytes

The human hepatocytes used for transplantation were hepatocytes (Lot No. BD85, from a 5-year-old boy) purchased from BD Gentest. The hepatocytes in a frozen state were thawed before use according to the known method (Chise Tateno et al., Near-completely humanized liver in mice shows human-type metabolic responses to drugs. Am J Pathol 165: 901-912, 2004).

The uPA-Tg/SCID mice at the age of 2 to 4 weeks were anesthetized with ether, an about 5-mm incision was made in the flank of each mouse, and $1.25 \times 10^5$ cells of the human hepatocytes were injected from the head of the spleen. After that, the spleen was returned to the peritoneal cavity and the incision was closed with a suture.

(1-3) Maintenance of Chimeric Mice

After transplantation, the recipient mice were maintained with free access to CRF-1 (Oriental Yeast Co., Ltd.) and tap water containing 0.012% of a sodium hypochlorite (Wako Pure Chemical Industries, Ltd.) solution.

Blood was collected weekly from each mouse via the tail vein, and the human albumin concentration in the mouse blood was measured by turbidimetric immunoassay using the latex reagent "Eiken ALB-II" manufactured by Eiken Chemical Co., Ltd. The measurement conditions were as described in the manual attached to the reagent.

(2) Administration of Inosinic Acid

On the day before the start of dietary administration, the body weights of the chimeric mice with human hepatocytes were measured. Those weighing 18.5 to 23.8 g were used for dietary administration. The blood human albumin concentrations at 13 days after the start of dietary administration were 12.7 to 17.5 mg/mL. These albumin concentrations indicate that the rates of human hepatocyte replacement were 85 to 94%. Little change was found in the blood human albumin concentrations before and after dietary administration.

The primary chimeric mice (16 mice in total) were allowed free access to a CRF-1 (Oriental Yeast Co., ltd.) diet supplemented with 1% inosinic acid (IA) for 3 days, a 3% IA-supplemented diet for 3 days, a 6% IA-supplemented diet for 2 days, and a 9% IA-supplemented diet for 6 days. The total IA intake was 88 g/kg body weight. The mice were given free access to tap water containing 0.012% of a sodium hypochlorite solution as drinking water.

At 15 days and later after the start of the dietary administration, 14 mice of them were continuously allowed free access to the same 9% IA-supplemented diet as before, and 4 mice of them were allowed free access to a CRF-1 diet not supplemented with IA. The four mice were named dietary IA intake cessation animals.

(3) Measurement of Plasma Uric Acid Concentration

Figure 2:
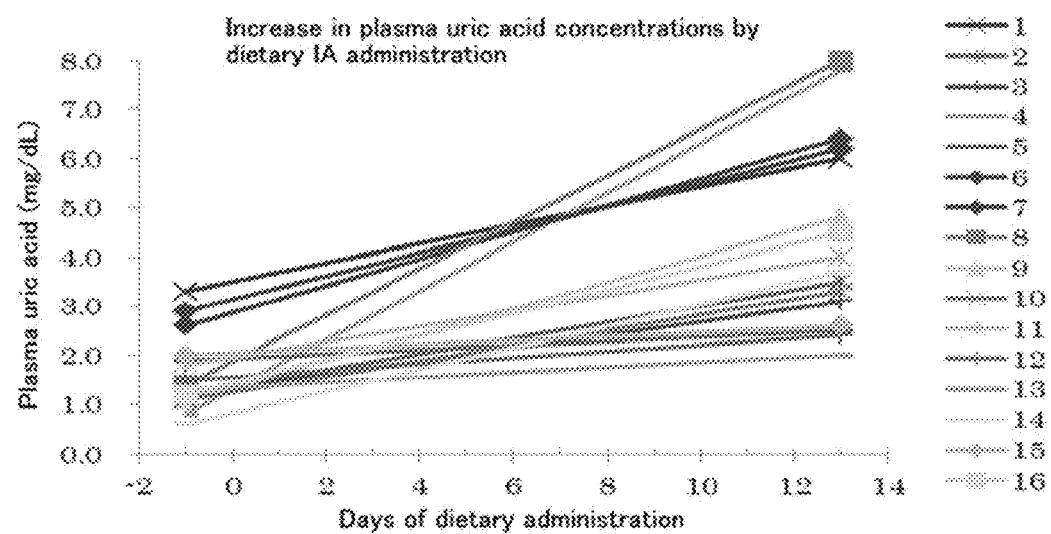
FIG. 2 shows a graph representing the time-course change in the plasma uric acid concentrations of primary chimeric mice during dietary inosinic acid (IA) administration.

The plasma uric acid levels were measured with DRI-CHEM 7000(FUJIFILM Corporation, Tokyo) on the day before the start of the dietary IA administration and 13 days after the start of the dietary IA administration. The results are shown in FIG. 2. The plasma uric acid concentrations were increased to 1.3- to 9.8-fold in all the 16 primary chimeric mice, and the plasma uric acid concentrations in 8 of the 16 primary chimeric mice reached 4 mg/dL or more.

Figure 3:
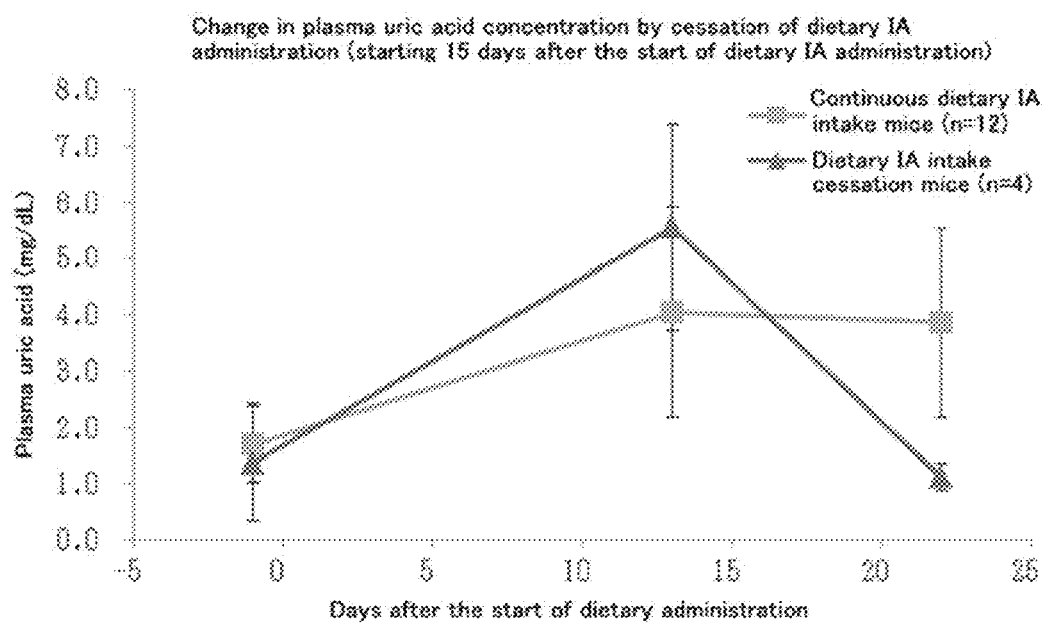
FIG. 3 shows a graph representing the time-course change in the plasma uric acid concentration in primary chimeric mice during dietary IA administration and the subsequent cessation period and in other primary chimeric mice during continuous dietary IA administration.
Figure 4:
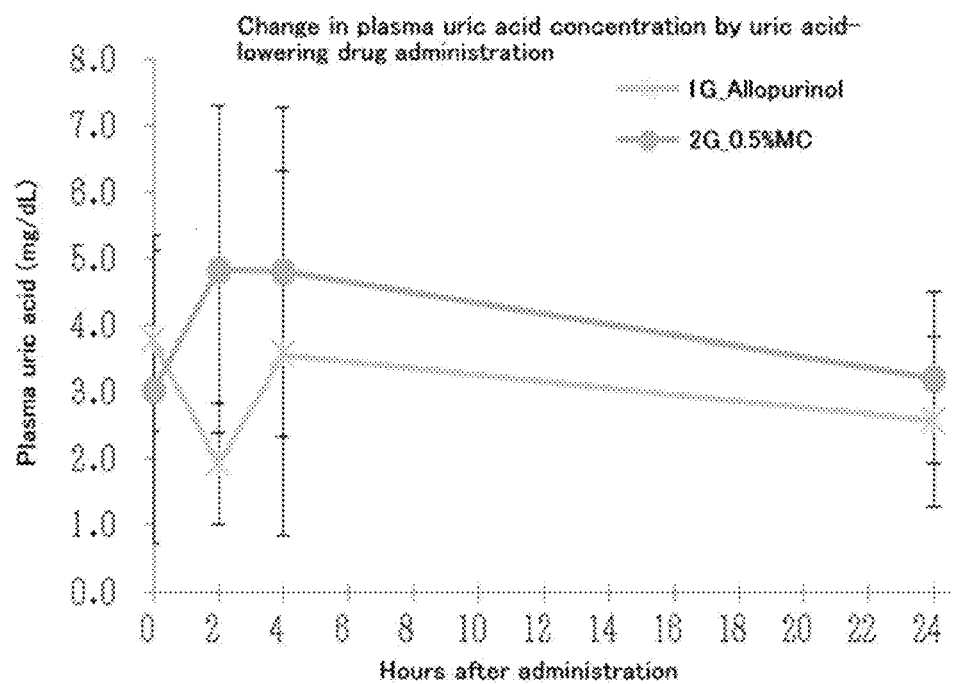
FIG. 4 shows a graph representing the time-course change in the plasma uric acid concentration after administration of the blood uric acid-lowering drug allopurinol to hyperuricemia model mice produced by dietary IA administration to primary chimeric mice.

FIG. 3 shows the mean of the plasma uric acid concentrations of the dietary IA intake cessation animals (animals were not fed the IA-supplemented diet at 15 days and later after the start of the dietary IA administration) and the mean of the plasma uric acid concentrations of the continuous dietary IA intake animals. The 12 continuous dietary IA intake animals were subjected to administration and blood collection as shown in FIGS. 4 at 14 and 15 days after the start of the dietary IA administration, but no influence was seen on the plasma uric acid concentrations. At 22days after the start of the dietary IA administration (i.e., 7 days after the start of dietary IA intake cessation), apparent difference was observed in the mean of the plasma uric acid levels between the two groups. This result also indicates that a hyperuricemia model can be produced by IA administration.

The total IA intake for the mice which had been allowed free access to the IA-supplemented diet for 22 days was 191 g/kg body weight. The total IA intake for the mice which had been allowed free access to the IA-supplemented diet for 28 days was 260 g/kg body weight.

These results demonstrate that feeding of chimeric mice carrying human hepatocytes with 1%, 3%, 6% or 9% IA-supplemented diets for 14 days in total resulted in the production of a hyperuricemia model having a plasma uric acid level of 4 mg/dL or more.

(4) Allopurinol Administration

<Hyperuricemia Model Animal Group>

The hyperuricemia model mice obtained as described above were subjected to administration of allopurinol, which is an existing drug for lowering blood uric acid levels. The number of the mice subjected to administration of allopurinol was six. On the day before the administration of allopurinol, all the six mice were confirmed to have plasma uric acid levels of 2.4to 6.0 mg/dL and body weights of 17.1 to 19.8 g and blood albumin concentrations of 12.7to 15.7 mg/mL (indicating that the rates of human hepatocyte replacement were 85 to 91%) and to be aged 130 to 152 days.

Allopurinol (Wako Pure Chemical Industries, Ltd.) was suspended in a 0.5 w/v% methylcellulose (MC) 400 solution (sterilized, Wako Pure Chemical Industries, Ltd.) for preparation of a 0.5 mg/mL allopurinol suspension. The 0.5 mg/mL allopurinol suspension was orally administered once in a volume of 10 mL/kg body weight (5 mg/kg body weight).

<Control Group>

For the control group (group of 6 mice), a 0.5 w/v% methylcellulose 400 solution, which was a vehicle for suspending allopurinol, was orally administered once in a volume of 10 mL/kg body weight to the hyperuricemia model mice obtained as described above. On the day before the administration of a 0.5 w/v% methylcellulose 400 solution, all the six hyperuricemia model mice were confirmed to have plasma uric acid levels of 2 to 8 mg/dL and body weights of 17.1 to 20.6 g and blood albumin concentrations of 12.7 to 15.4 mg/mL (indicating that the rates of human hepatocyte replacement were 85 to 90%) and to be aged 125 to 132 days.

(5) Allopurinol-Induced Change in Plasma Uric Acid Level

Blood was collected from each mouse before and 2, 4 and 24 hours after allopurinol or a 0.5 w/v % methylcellulose 400 solution was administered. The plasma uric acid concentration was measured in the same manner as above.

The results show that the mean of the plasma uric acid concentrations in the allopurinol administration group was 3.8 mg/dL before the administration and was 1.9 mg/dL at 2 hours after the administration, which indicates that the plasma uric acid concentration was significantly reduced by the administration of allopurinol. In contrast, the mean of the plasma uric acid concentrations in the control group was 3.0 mg/dL before the administration and was 4.8 mg/dL at 2 hours after the administration, which indicates that the administration of a 0.5 w/v % methylcellulose 400 solution resulted in no reduction in the plasma uric acid concentration.

The above results demonstrate that the hyperuricemia model of the present invention is applicable to screening for hyperuricemia therapeutic agents.

INDUSTRIAL APPLICABILITY

The model of the present invention is suitable for use in screening for hyperuricemia therapeutic agents, studies on the mechanism of hyperuricemia, etc.

The invention claimed is:

1. A mouse model of hyperuricemia obtained by:
   a) transplanting human hepatocytes into an immunodeficient mouse with liver dysfunction; and
   b) administering a diet containing about 1 to 10% by weight of an inosinic acid in a total amount of 30 g/kg body weight or more to the mouse obtained in step a) for about 7 to 28 days such that a mouse model of hyperuricemia is obtained that has:
   a liver containing 50% or more human hepatocytes,
   a body weight of about 80% or more of 19.4 g,
   a plasma or serum uric acid concentration of 4 mg/dL or more, and
   a concentration of human albumin of at least about 3.7 mg/mL or more.

2. The mouse model according to claim 1, wherein the inosinic acid is administered in a total amount of 40-80 to 350 g/kg body weight.

3. A method for screening agents, the method comprising:
   a) administering an agent to the mouse model of claim 1,
   b) comparing the plasma or serum concentration of uric acid in the mouse before and after administering the agent, and
   c) selecting an agent that lowers the plasma or serum concentration of uric acid after administering the agent.

4. The method according to claim 3, wherein the inosinic acid is administered in a total amount of 80 to 350 g/kg body weight.

5. The hyperuricemia mouse model of claim 1, wherein the human hepatocytes transplanted in step a) are obtained from an immunodeficient mouse with liver dysfunction that has been transplanted with human hepatocytes.

6. The hyperuricemia mouse model of claim 5, further comprising serially transplanting human hepatocytes into an immunodeficient mouse with liver dysfunction. OR
   wherein the immunodeficient mouse with liver dysfunction in step a) has been serially transplanted with human hepatocytes.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Artificial sequence
<220> FEATURE:
<223> OTHER INFORMATION: PCR primer

<400> SEQUENCE: 1
gggcggcggt accgatcctg agaacttcag ggtgag                36

<210> SEQ ID NO 2
<211> LENGTH: 36
<212> TYPE: DNA
<213> ORGANISM: Artificial sequence
<220> FEATURE:
<223> OTHER INFORMATION: PCR primer

<400> SEQUENCE: 2
gggcggcggt accaattctt tgccaaaatg atgaga                36